United States Patent [19]
Kawai et al.

[11] Patent Number: 5,811,596
[45] Date of Patent: Sep. 22, 1998

[54] METHOD OF PRODUCING FLUOROMETHYL 1,1,1,3,3,3-HEXAFLUOROISOPROPYL ETHER

[75] Inventors: Toshikazu Kawai; Mineo Watanabe, both of Saitama, Japan

[73] Assignee: Central Glass Co., Ltd., Yamaguchi, Japan

[21] Appl. No.: 945,044

[22] PCT Filed: Jan. 22, 1997

[86] PCT No.: PCT/JP97/00129

§ 371 Date: Oct. 20, 1997

§ 102(e) Date: Oct. 20, 1997

[87] PCT Pub. No.: WO97/30961

PCT Pub. Date: Aug. 28, 1997

[30] Foreign Application Priority Data

Feb. 21, 1996 [JP] Japan ...................................... 8-33339

[51] Int. Cl.⁶ .................................................... C07C 41/00
[52] U.S. Cl. .............................................................. 568/683
[58] Field of Search ..................................... 568/681, 683

[56] References Cited

FOREIGN PATENT DOCUMENTS 7-502037 3/1995 Japan .
WO 93/12057 6/1993 WIPO .

*Primary Examiner*—Gary Geist
*Assistant Examiner*—Karl J. Puttlitz, Jr.
*Attorney, Agent, or Firm*—Evenson, McKeown, Edwards & Lenahan, P.L.L.C.

[57] ABSTRACT

The present invention provides a novel method of producing fluoromethyl 1,1,1,3,3,3-hexafluoroisopropyl ether. It is a method of producing fluoromethyl 1,1,1,3,3,3-hexafluoroisopropyl ether by bringing a polyether represented by the following general formula (1) into contact with a medium comprising hydrogen fluoride and an accelerant, $$R^1O(CH_2O)_nR^2 \qquad (1)$$

where $R^1$ and $R^2$ are independently hydrogen, $C_1$–$C_{10}$ alkyl or haloalkyl groups, where halogen is fluorine, chlorine or bromine, n is an integer of from 1 to 10, and both of $R^1$ and $R^2$ are not hydrogen at the same time.

10 Claims, No Drawings

METHOD OF PRODUCING FLUOROMETHYL 1,1,1,3,3,3-HEXAFLUOROISOPROPYL ETHER

TECHNOLOGICAL FIELD

The present invention relates to a method of producing fluoromethyl 1,1,1,3,3,3-hexafluoroisopropyl ether, which is widely used as pharmaceutical and agrichemical products or intermediates thereof.

BACKGROUND TECHNOLOGY

As methods of producing fluoromethyl 1,1,1,3,3,3-hexafluoroisopropyl ether, there are known a method in which a mixture of concentrated sulfuric acid, hydrogen fluoride, paraformaldehyde and 1,1,1,3,3,3-hexafluoroisopropyl alcohol (hereinafter referred to as "HFIPA") is heated, and then the generated gas is trapped (U.S. Pat. No. 4,469,898), and another method in which trioxane is added to hydrogen fluoride, and then HFIPA is added thereto (JP-T-7-502037), and other methods. However, various kinds of polyethers are produced as by-products, or their yields are very low. These polyethers are separated from fluoromethyl 1,1,1,3,3,3-hexafluoroisopropyl ether by distillation, and then are discarded.

Furthermore, there is also known a method in which chloromethyl-1,1,1,3,3,3-hexafluoroisopropyl ether is fluorinated by potassium fluoride at high temperature and high pressure. However, the reaction conditions are severe, and furthermore the yield is merely 60%.

DISCLOSURE OF THE INVENTION

The present inventors have examined a method of producing fluoromethyl 1,1,1,3,3,3-hexafluoroisopropyl ether from formaldehyde or its polymer in high yield. With this, we found that it is possible to produce fluoromethyl 1,1,1,3,3,3-hexafluoroisopropyl ether from a polyether represented by the general formula (1):

$$R^1O(CH_2O)_nR^2 \quad (1)$$

where $R^1$ and $R^2$ are independently hydrogen, $C_1$–$C_{10}$ alkyl or haloalkyl groups (halogen is fluorine, chlorine or bromine), n is an integer of from 1 to 10, and both of $R^1$ and $R^2$ are not hydrogen at the same time). Thus, we achieved the present invention.

That is, the present invention provides a method of producing fluoromethyl 1,1,1,3,3,3-hexafluoroisopropyl ether by bringing a polyether represented by the general formula (1) into contact with a medium comprising hydrogen fluoride and an accelerant, $$R^1O(CH_2O)_nR^2 \quad (1)$$

where $R^1$, $R^2$ and n are the same as above.

Furthermore, the present invention provides a method of producing fluoromethyl 1,1,1,3,3,3-hexafluoroisopropyl ether by bringing a polyether represented by the general formula (1) and optionally 1,1,1,3,3,3-hexafluoroisopropyl alcohol into contact with a medium comprising hydrogen fluoride, an accelerant and optionally formaldehyde.

Concrete examples of $R^1$ and $R^2$ are alkyl groups such as methyl, ethyl, n-propyl, i-propyl, n-butyl, sec-butyl, t-butyl, pentyl, hexyl, heptyl and octyl, and residues which are isomers thereof, although they are not exemplified.

Furthermore, examples of the haloalkyl groups, in which fluorine and/or chlorine has been substituted for at least one hydrogen of these alkyl groups, are fluoromethyl, difluoromethyl, trifluoromethyl, fluoroethyl, difluoroethyl, 1-fluoroisopropyl, 1,1- difluoroisopropyl, 1,1,1-trifluoroisopropyl, 1,1,1,2-tetrafluoro-isopropyl, pentafluoroisopropyl, hexafluoroisopropyl, and the like.

It is particularly preferable that at least one of $R^1$ and $R^2$ is fluoromethyl group or hexafluoroisopropyl group.

Polyoxymethylene group is represented by a straight chain in the general formula, but it may be in the form of ring. It is not necessary to particularly limit the unit number (n) of oxymethylene group. However, if it is too large, its behavior will become substantially similar to that of formaldehyde polymer in case that the present invention's method is applied. Thus, it becomes necessary to increase the amount of the after-mentioned HFIPA to be added. With this, the use of a polyether of the general formula (1) does not make sense very much.

Concrete examples of polyethers of the general formula (1), which are preferably applied to the present invention's method, are:

$(CF_3)_2CHO(CH_2O)_nCH(CF_3)_2$ where n is an integer of from 1 to 10, $(CF_3)_2CHO(CH_2O)_nCH_2F$ where n is an integer of from 1 to 10, and $(CF_3)_2CHO(CH_2O)_nCH_3$ where n is an integer of from 1 to 10.

Particularly preferable ones are:

$(CF_3)_2CHO(CH_2O)_aCH(CF_3)_2$ where a is an integer of from 1 to 7, $(CF_3)_2CHO(CH_2O)_bCH_2F$ where b is an integer of from 1 to 6, and $(CF_3)_2CHO(CH_2O)_cCH_3$ where c is an integer of from 1 to 4.

Furthermore, these polyethers may be in the form of mixture.

The method of producing polyether of the general formula (1) is not limited, and its production method is nonlimitatively exemplified, as follows.

(a) An alcohol, represented by a general formula of $R^3$—OH where $R^3$ is a $C_1$–$C_{10}$ alkyl or haloalkyl group (halogen is fluorine, chlorine or bromine), is reacted with formaldehyde or its polymer, in the presence of a dehydrator such as sulfuric acid, thereby to obtain $R^3O(CH_2O)_nR^4$, where $R^3$ is the same as above, $R^4$ is hydrogen, $CH_3$ or $R^3$, and n is an integer of from 1 to 10.

(b) An alcohol, represented by a general formula of $R^3$—OH where $R^3$ is the same as above, and chloromethyl ether, represented by $R^4O(CH_2O)_nCH_2Cl$ where $R^4$ is the same as above, are brought into contact with a base such as caustic soda, thereby to obtain $R^4O(CH_2O)_nCH_2OR^3$ where $R^3$, $R^4$ and n are the same as above.

(c) HFIPA, formaldehyde and hydrogen fluoride are reacted together in the presence of a dehydrator such as sulfuric acid, thereby to obtain it as a by-product in the synthesis of fluoromethyl 1,1,1,3,3,3-hexafluoroisopropyl ether.

For example, a polyether of the general formula (1), where $R^1$ is hexafluoroisopropyl group, $R^2$ is methyl group, and n is 1, is obtained by the method (a) wherein HFIPA and formaldehyde and according to need methanol are reacted together, in the presence of a dehydrator such as sulfuric acid, or by the method (b) wherein HFIPA and chloromethyl methyl ether are treated with a base such as caustic soda.

According to a method of the present invention, a polyether represented by the general formula (1) is brought into contact with hydrogen fluoride, in the presence of a dehydrator as accelerant. Depending on the type of polyether, it is also preferable to allow HFIPA and/or formaldehyde or its polymer to coexist therewith.

Examples of the accelerant are Brφnsted acids, such as fuming sulfuric acid, concentrated sulfuric acid, sulfuric acid, fluorosulfuric acid, phosphoric acid anhydride, phosphoric acid and trifluoromethane sulfonic acid, and Lewis acids, such as titanium tetrachloride, aluminum chloride, antimony pentachloride, aluminum trifluoride, sulfuric anhydride and antimony pentafluoride. Of these, fuming sulfuric acid, concentrated sulfuric acid, a sulfuric acid having a concentration of at least 80 wt %, fluorosulfuric acid, phosphoric acid and the like or mixtures of these are preferable.

The reaction temperature is not particularly limited, and ranges from 10 to 100 ° C., preferably from 35 to 80 ° C. Within this temperature range, it is possible to distill the formed fluoromethyl 1,1,1,3,3,3-hexafluoroisopropyl ether, together with the unreacted raw materials, out of the reaction system, and thus this is preferable. If it is less than 10° C., the reaction becomes impractically slow. If it exceeds 100° C., the reaction becomes too fast. With this, it becomes difficult to control the reaction, and thus this is not preferable. The reaction pressure is not particularly limited, because it has little impact on the reaction. It is generally from 1 to 10 kg/cm$^2$.

Formaldehyde may be in a form which is generally industrially available, for example, its polymers such as paraformaldehyde and trioxane, and thus in the present specification these are referred to as simply formaldehyde.

The amount of each reagent in the method of the present invention depends on the end-group type of polyether, and, in case of mixture, on its compositional ratio. In the whole composition of the reagents, the molar ratio of the total number of moles of hexafluoroisopropyl group or optionally HFIPA (hereinafter referred to as "mole number of HFIPA") to the total number of moles of oxymethylene group and optionally fluoromethyl group or formaldehyde (hereinafter referred to as "mole number of formaldehyde") is from 0.5 to 5, preferably from 0.7 to 3. If it is not greater than 0.5, the yield of fluoromethyl 1,1,1,3,3,3-hexafluoroisopropyl ether lowers. This is not preferable in practice. If it is not less than 5, the conversion of HFIPA lowers. This is not preferable, because the efficiency of using it decreases.

It is generally preferable that hydrogen fluoride exists in stoichiometrically excess of "the number of moles of formaldehyde".

The molar ratio of that to formaldehyde is preferably from 1 to 50, more preferably from 3 to 30. If it is not greater than 1, the reaction becomes slow. This is not preferable, because the yield lowers. Even if it is not less than 50, this does not cause problems in terms of the reaction. This is not, however, particularly advantageous, because this is accompanied by the increase of the amount of the unreacted hydrogen fluoride to be distilled out, the increase of the size of equipment, and the like. The molar ratio of the accelerant to formaldehyde is from 0.5 to 20, preferably from 0.7 to 5.0. If it is not greater than 0.5, the reaction rate lowers. Not less than 20 will do, but is not preferable economically.

According to the method of the present invention, the order of the addition of each reagent is not particularly limited. For example, there is a method in which polyether and optionally HFIPA are gradually added to where a mixture prepared by previously mixing the accelerant, hydrogen fluoride and optionally formaldehyde is maintained at a certain predetermined temperature, or another method in which the accelerant, hydrogen fluoride and polyether and optionally formaldehyde and/or HFIPA are previously mixed together at a temperature not higher than 10 ° C., followed by a gradual increase of the temperature to a certain predetermined temperature. In either case, the reaction product is allowed to flow out to the outside, while relatively high boiling point components are refluxed to the reactor from the generated gas, using a condenser. The gas component, which flowed out, is condensed, and then, in case that it is accompanied by acid, is subjected to the steps of neutralization, washing with water, drying and the like, followed by distillation, thereby to obtain the aimed fluoromethyl 1,1,1,3,3,3-hexafluoroisopropyl ether.

According to the method of the present invention, it is possible to efficiently produce fluoromethyl 1,1,1,3,3,3-hexafluoroisopropyl ether from polyether. Furthermore, it is possible to produce fluoromethyl 1,1, 1,3,3,3-hexafluoroisopropyl ether from fluorinated polyethers which have been discarded in the past as by-products in the production of fluoromethyl 1,1,1,3,3,3-hexafluoroisopropyl ether. With this, it produces substantial results that the production cost can substantially be reduced.

THE BEST MODE TO CARRY OUT THE INVENTION

In the following, there are shown examples of the embodiments of the present invention, to which the scope of the present invention is not limited. The gas chromatographic analysis was conducted in accordance with the following conditions, and % represents area %. The recovery is a referential value obtained by assuming area %=weight %.

Gas Chromatograph: Hewlett Packard HP-5890 seriesII

Column: Halomatics-624 (30 m×0.32 mmID×3 μm)

Column Temperature: 40° C.(10 minutes maintenance) - 200° C. (temperature increase rate 10° C. /min)

Injection Port Temperature: 200° C.

Carrier Gas: He 40 kPa

Sample: 0.5 μl

Split Ratio: 1/80

Detector: FID 200° C.

Integrator: Hewlett Packard HP-3396 seriesII

[Referential Example 1]

Synthesis of $(CF_3)_2CHOCH_2OCH(CF_3)_2$

A 300 ml reactor, which had been cooled down in dry ice/acetone bath to −20° C., was charged with 111.3 g of fuming sulfuric acid, 9.3 g of paraformaldehyde and 52.8 g of HFIPA, followed by stirring for 20 minutes. After stopping stirring, it was cooled down to room temperature by standing still. With this, the contents were separated into two layers. The organic matter of the upper layer was taken out and then washed with 50 ml of 5% sodium hydrogencarbonate aqueous solution. With this, it was separated into two layers to obtain an organic matter.

The obtained organic matter was distilled under reduced pressure, and a distillate under a degree of vacuum of from 71 to 73 mmHg and a distillation temperature of 55° C. was recovered as a main distillate. With this, 21.0 g of $(CF_3)_2CHOCH_2OCH(CF_3)_2$ (a purity of 99.9%) was obtained. The molecular structure was determined by GC-MASS, $^1$H-NMR and $^{19}$F-NMR spectrums.

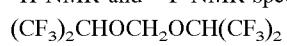

Mass Spectrum

| M+ | 348 |
|---|---|
| $(CF_3)_2CHOCH_2$ | 181 |
| $(CF_3)_2CH$ | 151 |
| $CF_3$ | 69 |

NMR(TMS, $CFCl_3$ basis)

| $CH_2$ | δ 5.2 ppm(singlet 2H) |
|---|---|
| CH | δ 4.5 ppm(multiplet 2H) |
| $CF_3$ | −73.8 ppm ($J_{H-F}$ 8.3 Hz doublet) |

[Referential Example 2]

Synthesis of $(CF_3)_2CHO(CH_2O)_2CH(CF_3)_2$

A 500 ml four-neck flask was charged with 44.5 g of paraformaldehyde, and then 120 ml of 98% sulfuric acid was added thereto with stirring under cooling with ice. While it was maintained at a temperature of up to 5° C., 127.5 g of HFIPA was added thereto. Under this condition, the reaction was continued for 1 hr. Then, a crystal, which had deposited during the reaction, was separated by filtration using a glass filter. The obtained crystal was washed with 200 ml of water, then dissolved into 1.2 L of methylene chloride, and then dried with 50 g of anhydrous magnesium sulfate. After drying, methylene chloride was distilled off, thereby to obtain 126.9 g of $(CF_3)_2CHO(CH_2O)_2CH(CF_3)_2$ (a purity of 99.6%). The melting point was measured, and it was 54.3° C. The molecular structure was determined by GC-MASS, $^1$H-NMR and $^{19}$F-NMR spectrums.

$CF_3)_2CHO(CH_2O)_2CH(CF_3)_2$
Mass Spectrum

| M+ | 378 |
|---|---|
| $(CF_3)_2CH(OCH_2)_2$ | 211 |
| $(CF_3)_2CHOCH_2$ | 181 |
| $CF_3$ | 69 |

NMR(TMS, $CFCl_3$ basis)

| $CH_2$ | δ 5.0 ppm(singlet 4H) |
|---|---|
| CH | δ 4.4 ppm($J_{H-F}$ 5.9 Hz septet 1H) |
| $CF_3$ | −74.5 ppm ($J_{H-F}$ 6.0 Hz doublet 3F) |

[Referential Example 3]

Synthesis of $(CF_3)_2CHOCH_2OCH_3$

A 500 ml four-neck flask was charged with 293 g of 15%—NaOH aqueous solution, followed by stirring. Then, 168 g of HFIPA was added thereto, followed by cooling to 10° C. 120.8 g of chloromethyl methyl ether was added thereto by spending about 1 hr, while the temperature was maintained within a range of from 10 to 12° C. Then, stirring was continued for 30 minutes. Of the separated two layers, the organic layer was taken out and then washed with 200 ml of water, thereby to obtain 37.2 g of an organic matter which is $(CF_3)_2CHOCH_2OCH_3$ of a purity of 97.5%. This was distilled, and a distillate at a distillation temperature of from 76 to 77° C. was recovered as a main distillate. With this, 27.5 g of $(CF_3)_2CHOCH_2OCH_3$ (a purity of 99.2%) was obtained. The molecular structure was determined by GC-MASS, $^1$H-NMR and $^{19}$F-NMR spectrums.

$(CF_3)_2CHOCH_2OCH_3$
Mass Spectrum

| M+ − 1 | 211 |
|---|---|
| $(CF_3)_2CHOCH_2$ | 181 |
| $CF_3$ | 69 |
| $CH_3OCH_2$ | 45 |

NMR(TMS, $CFCl_3$ basis)

| $CH_3$ | δ 3.4 ppm(singlet 3H) |
|---|---|
| $CH_2$ | δ 4.8 ppm(singlet 2H) |
| CH | δ 4.4 ppm(multiplet 1H) |
| $CF_3$ | −74.5 ppm ($J_{H-F}$ 5.8 Hz doublet 3F) |

[Referential Example 4]

A 5L stainless steel reactor was charged with 500 ml of 98% sulfuric acid, 1,000 g of hydrogen fluoride and 300 g of paraformaldehyde. This reaction mixture was heated to 65° C., with stirring. Then, 1,680 g of HFIPA was added dropwise thereto by spending 2 hr. Steam which had been generated by the reaction was collected by a water-containing trap. Then, of the separated two-layers, the organic layer was take out and then washed, thereby to obtain 1,410 g of an organic matter. From this organic matter, fluoromethyl 1,1,1,3,3,3-hexafluoroisopropyl ether was distilled away. With this, 160 g of polyethers which are by-products were obtained as residue.

This residue was analyzed by gas chromatography and MASS, and thus it was found as follows.

| $(CF_3)_2CHO(CH_2O)_aCH(CF_3)_2$ | (a = 1–7, main component a = 1,2) | 55.9% |
|---|---|---|
| $(CF_3)_2CHO(CH_2O)_bCH_2F$ | (b = 1–6, main component b = 1,2) | 31.9% |
| $(CF_3)_2CHO(CH_2O)_cCH_3$ | (c = 1–4, main component c = 1) | 1.6% |

[EXAMPLE 1]

A 1 L stainless steel reactor was charged with 75 g of 98% sulfuric acid, 196 g of hydrogen fluoride, and 124 g of polyethers obtained in the Referential Example 4, followed by gradual heating to 65° C. by spending 4 hr. Steam, which had been generated by the reaction, was collected by a water-containing trap. Then, the obtained organic layer was washed with water, thereby to obtain 126 g of an organic matter.

The obtained organic matter was analyzed by gas chromatography, and thus it was found that this organic matter contained 96.1% of fluoromethyl 1,1,1,3,3,3-hexafluoroisopropyl ether. By the distillation of this organic matter, 107 g of fluoromethyl 1,1,1,3,3,3-hexafluoroisopropyl ether (a purity of 99.9%) was obtained.

[EXAMPLE 2]

A 200 ml stainless steel reactor was charged with 34.8 g of $(CF_3)_2CHOCH_2OCH(CF_3)_2$ obtained in Referential Example 1, 3 g of paraformaldehyde, 30 g of hydrogen fluoride, and 25 g of fuming sulfuric acid, followed by gradual heating to 55° C. by spending 2 hr. Steam, which had been generated by the reaction, was collected by a water-containing trap, and the obtained organic layer was washed with water, thereby to obtain 35.3 g of an organic matter. This organic matter was analyzed by gas chromatography, and thus this organic matter was found to contain 95.3% of fluoromethyl 1,1,1,3,3,3-hexafluoroisopropyl ether (a yield of 84.1%).

[EXAMPLE 3]

A 200 ml stainless steel reactor was charged with 37.8 g of $(CF_3)_2CHO(CH_2O)_2CH(CF_3)_2$ obtained in Referential Example 2, 30 g of hydrogen fluoride, and 25 g of fuming sulfuric acid, followed by gradual heating to 55° C. by spending 2 hr. Steam, which had been generated by the reaction, was collected by a water-containing trap, and the obtained organic layer was washed with water, thereby to obtain 37.0 g of an organic matter. This organic matter was analyzed by gas chromatography, and thus it was found to contain 94.6% of fluoromethyl 1,1,1,3,3,3-hexafluoroisopropyl ether (a yield of 87.5%).

[EXAMPLE 4]

A 200 ml stainless steel reactor was charged with 21.2 g of $(CF_3)_2CHOCH_2OCH_3$ obtained in Referential Example 3, 60 g of hydrogen fluoride, and 25 g of fuming sulfuric acid, followed by gradual heating to 50° C. by spending 4 hr. Steam, which had been generated by the reaction, was collected by a water-containing trap, and the obtained organic layer was washed with water, thereby to obtain 18.3 g of an organic matter. This organic matter was analyzed by gas chromatography, and thus it was found to contain 89.0% of fluoromethyl 1,1,1,3,3,3-hexafluoroisopropyl ether (a yield of 81.4%).

[EXAMPLE 5]

A 1 L stainless steel reactor was charged with 76 g of dimethoxymethane ($CH_3OCH_2OCH_3$), 120 g of hydrogen fluoride, 40 g of 98% sulfuric acid and 168 g of HFIPA, followed by gradual heating to 50° C. by spending 6 hr. Steam, which had been generated by the reaction, was collected by a water-containing trap, and to the thus obtained aqueous solution calcium chloride was added, thereby to form two layers. Then, the organic layer obtained by separation was washed with water, thereby to obtain 218.5 g of an organic matter. This organic matter was analyzed by gas chromatography, and thus it was found to contain 45.7% of fluoromethyl 1,1,1,3,3,3-hexafluoroisopropyl ether (a yield of 49.9%).

We claim:

1. A method of producing fluoromethyl 1,1,1,3,3,3-hexafluoroisopropyl ether by bringing a polyether represented by the following general formula (1) into contact with a medium comprising hydrogen fluoride and an accelerant, $$R^1O(CH_2O)_nR^2 \qquad (1)$$

where $R^1$ and $R^2$ are independently hydrogen, $C_1$–$Cl_{10}$ alkyl or haloalkyl groups, where halogen is fluorine, chlorine or bromine, n is an integer of from 1 to 10, and both of $R^1$ and $R^2$ are not hydrogen at the same time.

2. A method of producing fluoromethyl 1,1,1,3,3,3-hexafluoroisopropyl ether by bringing a polyether represented by the following general formula (1) and optionally 1,1,1,3,3,3-hexafluoroisopropyl alcohol into contact with a medium comprising hydrogen fluoride, an accelerant and optionally formaldehyde, $$R^1O(CH_2O)_nR^2 \qquad (1)$$

where $R^1$ and $R^2$ are independently hydrogen, $C_1$–$C_{10}$ alkyl or haloalkyl groups, where halogen is fluorine, chlorine or bromine, n is an integer of from 1 to 10, and both of $R^1$ and $R^2$ are not hydrogen at the same time.

3. A method of producing fluoromethyl 1,1,1,3,3,3-hexafluoroisopropyl ether according to claim 1, which is characterized in that said accelerant is fuming sulfuric acid, concentrated sulfuric acid, sulfuric anhydride, a sulfuric acid having a concentration of at least 80 wt %, or a fluorosulfuric acid.

4. A method of producing fluoromethyl 1,1,1,3,3,3-hexafluoroisopropyl ether according to claim 1, which is characterized in that said contact is conducted at a temperature of from 10 to 100° C.

5. A method of producing fluoromethyl 1,1,1,3,3,3-hexafluoroisopropyl ether according to claim 1, which is characterized in that said polyether represented by the general formula (1)is polymethyleneglycol bishexafluoroisopropyl ether $(CF_3)_2CHO(CH_2O)_aCH(CF_3)_2$ where a is an integer of from 1 to 7.

6. A method of producing fluoromethyl 1,1,1,3,3,3-hexafluoroisopropyl ether according to claim 1, which is characterized in that said polyether represented by the general formula (1) is bishexafluoroisopropoxymethane $(CF_3)_2CHOCH_2OCH(CF_3)_2$.

7. A method of producing fluoromethyl 1,1,1,3,3,3-hexafluoroisopropyl ether according to claim 1, which is characterized in that said polyether represented by the general formula (1) is polymethyleneglycol fluoromethyl hexafluoroisopropyl ether $(CF_3)_2CHO(CH_2O)_bCH_2F$ where b is an integer of from 1 to 6.

8. A method of producing fluoromethyl 1,1,1,3,3,3-hexafluoroisopropyl ether according to claim 1, which is characterized that said polyether represented by the general formula (1) is fluoromethoxymethyl hexafluoroisopropyl ether $(CF_3)_2CHOCH_2OCH_2F$.

9. A method of producing fluoromethyl 1,1,1,3,3,3-hexafluoroisopropyl ether according to claim 1, which is characterized in that said polyether represented by the general formula (1) is polymethyleneglycol methylhexafluoroisopropyl ether$(CF_3)_2CHO(CH_2O)_cCH_3$ where c is an integer of from 1 to 4.

10. A method of producing fluoromethyl 1,1,1,3,3,3-hexafluoroisopropyl ether according to claim 1, which is characterized in that said polyether represented by the general formula (1) is methoxymethyl hexafluoroisopropyl ether $(CF_3)_2CHO\ CH_2OCH_3$.

* * * * *